United States Patent
Lee et al.

(10) Patent No.: US 9,726,603 B2
(45) Date of Patent: Aug. 8, 2017

(54) GRATING PATTERN ELEMENT, TARGET MATERIAL MEASURING APPARATUS, AND TARGET MATERIAL MEASURING METHOD

(71) Applicant: SAMSUNG ELECTRONICS CO., LTD., Suwon-si (KR)

(72) Inventors: Joonhyung Lee, Yongin-si (KR); Sangkyu Kim, Yongin-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/809,374

(22) Filed: Jul. 27, 2015

(65) Prior Publication Data

US 2016/0131642 A1    May 12, 2016

(30) Foreign Application Priority Data

Nov. 11, 2014 (KR) .................. 10-2014-0156248

(51) Int. Cl.
*G01N 21/47* (2006.01)
*A61B 10/00* (2006.01)
*A61B 5/00* (2006.01)
*G01N 33/543* (2006.01)

(52) U.S. Cl.
CPC ....... *G01N 21/4788* (2013.01); *A61B 5/4261* (2013.01); *A61B 10/0064* (2013.01); *G01N 33/54373* (2013.01); *G01N 2021/4735* (2013.01)

(58) Field of Classification Search
CPC ................ G01N 21/4788; G01N 33/54373
See application file for complete search history.

(56) References Cited

U.S. PATENT DOCUMENTS

| | | | | |
|---|---|---|---|---|
| 4,352,983 A | * | 10/1982 | Silvus, Jr. | G01N 21/431 250/227.25 |
| 4,647,544 A | * | 3/1987 | Nicoli | G01N 21/4788 250/461.1 |
| 2008/0163674 A1 | * | 7/2008 | Bonne | G01N 1/40 73/31.05 |
| 2008/0215073 A1 | * | 9/2008 | Iwanaga | C12N 5/0062 606/151 |
| 2011/0223688 A1 | * | 9/2011 | Sinclair | G01N 21/7743 436/501 |
| 2011/0239759 A1 | | 10/2011 | Cobianu et al. | |
| 2013/0165329 A1 | * | 6/2013 | Vartak | G01N 21/253 506/9 |
| 2014/0057840 A1 | | 2/2014 | Kodama et al. | |

FOREIGN PATENT DOCUMENTS

| | | |
|---|---|---|
| JP | 2005127827 A | 5/2005 |
| JP | 2005308472 A | 11/2005 |
| KR | 100705743 B1 | 4/2007 |

* cited by examiner

*Primary Examiner* — Paul Hyun
(74) *Attorney, Agent, or Firm* — Sughrue Mion, PLLC (57) ABSTRACT

A grating pattern element includes peaks which are periodically arranged and valleys provided between the peaks, and at least one of the peaks and at least one of the valleys includes an adsorbing material on a surface thereof which adsorbs a target material.

11 Claims, 7 Drawing Sheets

GRATING PATTERN ELEMENT, TARGET MATERIAL MEASURING APPARATUS, AND TARGET MATERIAL MEASURING METHOD

RELATED APPLICATION

This application claims priority from Korean Patent Application No. 10-2014-0156248, filed on Nov. 11, 2014, in the Korean Intellectual Property Office, the disclosure of which is incorporated herein in its entirety by reference.

BACKGROUND

1. Field

The present disclosure relates to a grating pattern element, a target material measuring apparatus, and a target material measuring method capable of finding information indicating a target material provided on a surface of an object.

2. Description of the Related Art

States of various objects may be grasped by amounts of target materials that are distributed on surfaces of the objects. For example, whether skin is healthy may be determined by measuring secretions or secretion levels. Therefore, a technology of measuring an amount of a target material that exists on a surface of an object is required in various fields.

In the technology of measuring the amount of the target material provided on the surface of the object, a tape is attached to and detached from the skin and the amount of the target material with which the tape is stained may be measured or spectroscopic spectrum may be analyzed by irradiating magnetic resonance imaging (MIR).

SUMMARY

Provided is a grating pattern element capable of adsorbing a target material onto a surface of an object.

Provided are a target material measuring apparatus including a grating pattern element and a target material measuring method.

According to an aspect of an exemplary embodiment, a grating pattern element includes peaks which are periodically arranged and separate from one another and valleys provided between the peaks, such that at least one of each of the peaks and each of the valleys includes an adsorbing material on a surface thereof which adsorbs a target material.

The target material may be physisorbed or chemisorbed onto the adsorbing material.

The target material may include oil.

The adsorbing material may include a hydrophobic material.

One of each of the peaks and each of the valleys may include a hydrophobic material on a surface thereof and the other may include a hydrophilic material on a surface thereof.

The hydrophilic material may include at least one of $SiO_2$ and $TiO_2$ and the hydrophobic material may include at least one of polydimethylsiloxane (PDMS) and SU-8 photoresist.

According to an aspect of an exemplary embodiment, an apparatus for measuring an amount of a target material provided on a surface of an object includes a grating pattern element including a concavo-convex cross-section in which peaks and valleys are periodically arranged and at least one of each of the peaks and each of the valleys includes adsorbing material which adsorbs the target material provided on a surface thereof, a light source for emitting light and irradiating the grating pattern element with the light, a measuring unit for measuring intensities of diffraction patterns of light diffracted by the grating pattern element, and an information outputter for outputting information indicating the amount of the target material provided on the surface of the object from the intensities of the diffraction patterns of the diffracted light.

The target material may be physisorbed or chemisorbed onto the adsorbing material.

The target material may include oil.

The adsorbing material may include a hydrophobic material.

One of each of the peaks and each of the valleys may include a hydrophobic material on a surface thereof and the other may include a hydrophilic material on a surface thereof.

The hydrophilic material may include at least one of $SiO_2$ and $TiO_2$ and the hydrophobic material may include at least one of polydimethylsiloxane (PDMS) and SU-8 photoresist.

The measuring unit may measure at least one of intensities of a plurality of constructive interference patterns included in the diffraction patterns.

The information outputter may calculate an intensity ratio between two different constructive interference patterns among the plurality of constructive interference patterns.

One of the two different constructive interference patterns may be a (2m+1)th constructive interference pattern and the other may be a 2nth constructive interference pattern, where m and n are integers.

The light source may emit single-colored light to the grating pattern element.

A height difference between the peaks and the valleys may be smaller than ¼ of a wavelength of the light emitted by the light source.

According to an aspect of an exemplary embodiment, a target material measurement method includes contacting a surface of an object with a grating pattern element including a concavo-convex cross-section in which peaks and valleys are periodically arranged and at least one of each of the peaks and each of the valleys includes an adsorbing material which adsorbs the target material provided on a surface thereof, irradiating the grating pattern element with light, measuring intensities of diffraction patterns of light diffracted by the grating pattern element, and outputting information indicating the amount of the target material provided on the surface of the object from the intensities of the diffraction patterns of the diffracted light.

The target material may be physisorbed or chemisorbed onto the adsorbing material.

The target material may include oil.

The adsorbing material may include a hydrophobic material.

One of each of the peaks and each of the valleys may include a hydrophobic material on a surface thereof and the other may include a hydrophilic material on a surface thereof.

The measuring of intensities of diffraction patterns of light diffracted by the grating pattern element may include measuring at least one of intensities of a plurality of constructive interference patterns included in the diffraction patterns.

The outputting of the information indicating the amount of the target material provided on the surface of the object from the intensities of the diffraction patterns of the diffracted light may include calculating an intensity ratio between two different constructive interference patterns among the plurality of constructive interference patterns.

One of the two different constructive interference patterns may be a (2m+1)th constructive interference pattern and the other may be a 2nth constructive interference pattern, where m and n are integers.

The outputting of the information indicating the amount of the target material provided on the surface of the object from the intensities of the diffraction patterns of the diffracted light may include calculating a height difference between the peaks and the valleys from the intensities of the diffraction patterns.

A height difference between the peaks and the valleys may be smaller than ¼ of a wavelength of the light used to irradiate the grating pattern element.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

A grating pattern element, a target material measuring apparatus, and a target material measuring method according to exemplary embodiments will be described more fully hereinafter with reference to the accompanying drawings, in which elements of exemplary embodiments are shown. Exemplary embodiments may, however, be embodied in many different forms and should not be construed as limited to the exemplary embodiments set forth herein. Rather, these embodiments are provided so that this disclosure will be thorough and complete, and will fully convey the scope of exemplary embodiments to one of ordinary skill in the art. In the drawings, the thickness of layers and regions are exaggerated for clarity. It will also be understood that when a layer is referred to as being "on" another layer or substrate, it can be directly on the other layer or substrate, or intervening layers may also be present. The same reference numerals in different drawings represent the same element, and thus their description will be omitted.

Figure 1:
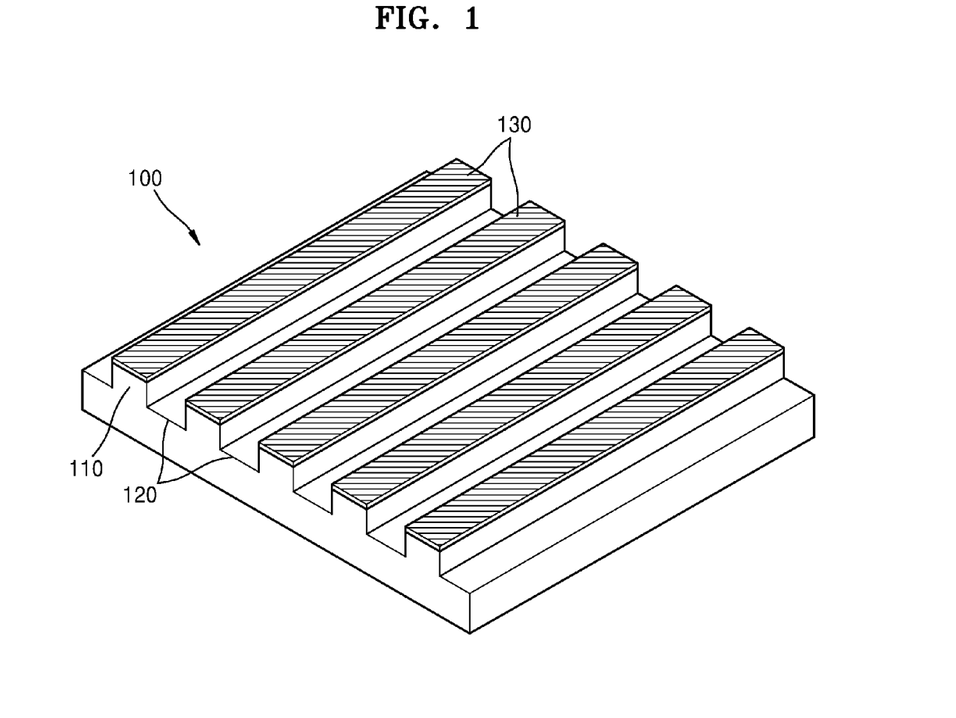
FIG. 1 is a view illustrating a grating pattern element according to an exemplary embodiment.

FIG. 1 is a view illustrating a grating pattern element 100 according to an exemplary embodiment. Referring to FIG. 1, the grating pattern element 100 may include peaks 110 which are periodically arranged and separate from one another and valleys 120 provided between the peaks 110. At least a pair of peaks 110 and valleys 120 may be formed. For example, more than four pairs of peaks 110 and valleys 120 may be formed. However, exemplary embodiments are not limited thereto. At least one of each of the peaks 110 and each of the valleys 120 may include an adsorbing material 130 which adsorbs a target material provided on a surface thereof. Here, the target material may mean a material to be measured on a surface of an object. For example, the target material may include oil and various materials such as an antigen, an antibody, and heavy metals other than the oil, which is only an exemplary embodiment. The target material may include various materials to be measured on the surface of the object.

The target material may be adsorbed onto adsorbing material 130. For example, the target material may be physisorbed or chemisorbed onto the adsorbing material 130. The adsorbing material 130 may include a hydrophobic material. However, exemplary embodiments are not limited thereto. The adsorbing material 130 may be provided on at least one surface of each of the peaks 110 and each of the valleys 120. In FIG. 1, the adsorbing material 130 is provided on the surfaces of the peaks 110. However, exemplary embodiments are not limited thereto. As described herein, the adsorbing material 130 may be provided on the surfaces of the valleys 120 or the surfaces of all the peaks 110 and the valleys 120.

Figure 2:
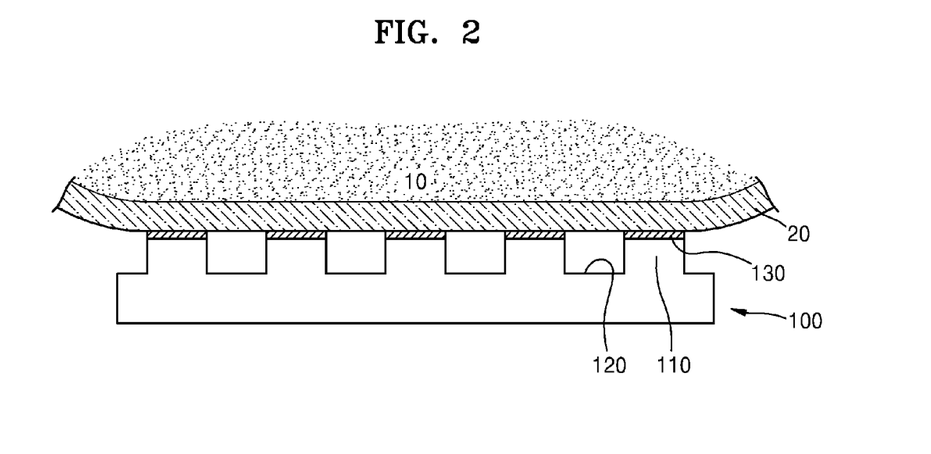
FIG. 2 is a view illustrating that the grating pattern element of FIG. 1 contacts a surface of an object.
Figure 3:
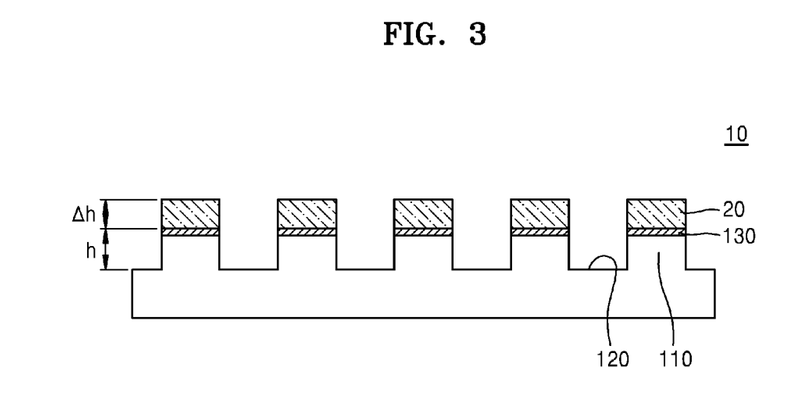
FIG. 3 is a view illustrating an example in which a target material provided on the surface of the object is adsorbed onto the adsorbing material of the grating pattern element.

FIG. 2 is a view illustrating that the grating pattern element 100 of FIG. 1 contacts a surface of an object 10. FIG. 3 is a view illustrating an example in which a target material 20 on the surface of the object 10 is adsorbed onto the adsorbing material 130 of the grating pattern element 100.

Referring to FIG. 2, when the grating pattern element 100 contacts the surface of the object 10, the adsorbing material 130 provided in the grating pattern element 100 may be adsorbed onto the target material 20 of the surface of the object 10. The object 10 may include an animal and a human body. However, exemplary embodiments are not limited thereto. The target material 20 provided on the surface of the object 10 may include the oil, the antigen, the antibody, and the heavy metals as described above. However, exemplary embodiments are not limited thereto. The adsorbing material 130 that adsorbs the target material 20 may include a hydrophobic material, a hydrophilic material, an antigen, and an antibody. However, exemplary embodiments are not limited thereto. FIG. 3 is a view illustrating the grating pattern element 100 after the contact process illustrated in FIG. 2 is performed. Referring to FIG. 3, the target material 20 may be adsorbed onto the adsorbing material 130 provided on the surfaces of the peaks 110. As illustrated in FIG. 3, the target material 20 is adsorbed onto the adsorbing material 130 so that a height h of the peaks 110 on whose surfaces the adsorbing material 130 is provided may change. That is, as illustrated in FIG. 3, the height of the peaks 110 may change from h to h+Δh. In addition, Δh may be dependent on an amount of the target material 20 provided on the surface of the object 10. Therefore, information indicating the amount of the target material 20 provided on the surface of the object 10 may be found through a change in height difference between the peaks 110 and the valleys 120 before and after the target material 20 contacts the object 10. Therefore, the grating pattern element 100 according to the exemplary embodiment may be used for measuring the amount of the target material 20 on the surface of the object 10. The height difference between the peaks 110 and the valleys 120 may be measured by various methods. For example, the height difference between the peaks 110 and the valleys 120 may be determined by measuring diffraction patterns 200 generated by irradiating the grating pattern element 100 with light, which will be described in more detail herein.

Figure 4:
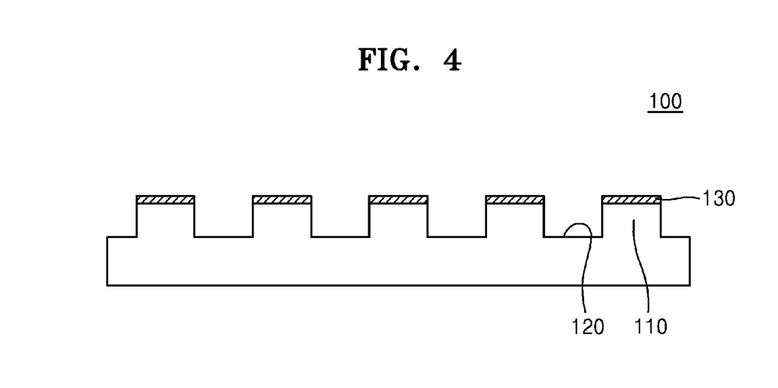
FIGS. 4 to 6 are cross-sectional views illustrating exemplary embodiments of the grating pattern element of FIG. 1.
Figure 5:
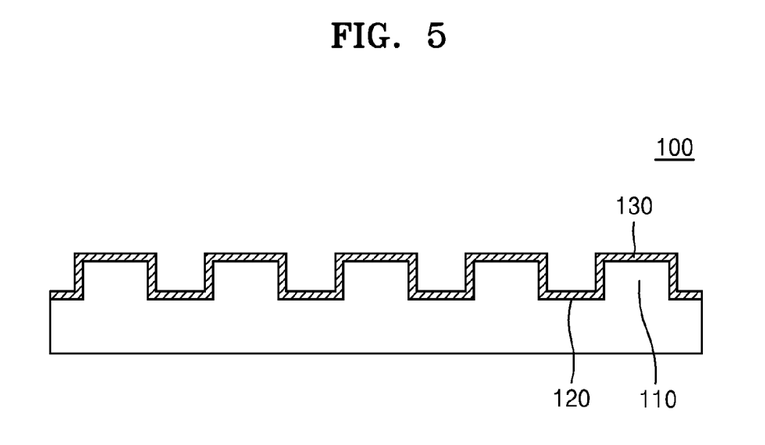
Figure 6:
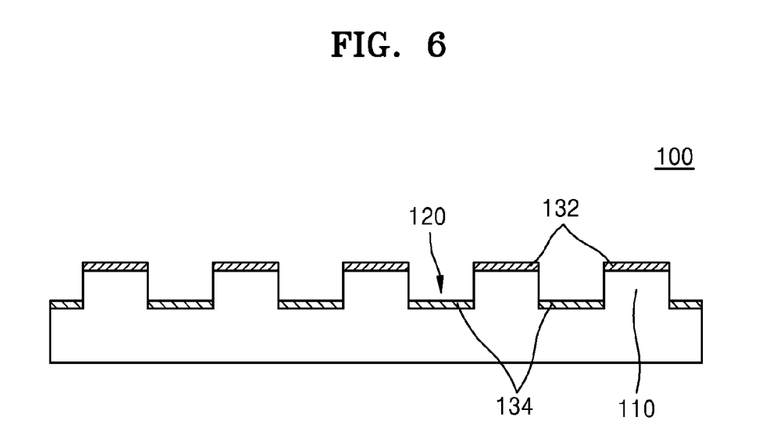

FIGS. 4 to 6 are cross-sectional views illustrating exemplary embodiments of the grating pattern element of FIG. 1.

Referring to FIGS. 4 and 5, at least one of each of the peaks 110 and each of the valleys 120 may include the adsorbing material 130 which adsorbs the target material provided on the surface thereof. As illustrated in FIG. 4, the peaks 110 may include the adsorbing material 130. In this case, the target material is adsorbed onto the adsorbing material 130 so that the height of the peaks 110 may change. Alternatively, as illustrated in FIG. 5, all of the peaks 110 and the valleys 120 may include the adsorbing material 130. In this case, when the grating pattern element 100 contacts the surface of the object, since the peaks 110 contact the surface of the object and the valleys 120 do not contact the surface of the object 10, target material is adsorbed onto the adsorbing material 130 of the peaks 110 so that the height of the peaks 110 may change. As described above, when the adsorbing material 130 is provided on the surfaces of all the peaks 110 and the valleys 120, it is not necessary to selectively coat the adsorbing material 130 during manufacturing of the grating pattern element 100. Therefore, manufacturing processes of the grating pattern element 100 may be simplified.

Referring to FIG. 6, one of each of the peaks 110 and each of the valleys 120 may include a hydrophobic material 132 as an adsorbing material provided on a surface thereof. In FIG. 6, it is illustrated that the peaks 110 between the peaks 110 and the valleys 120 include the hydrophobic material 132 on the surfaces thereof. However, exemplary embodiments are not limited thereto. For example, the valleys 120 may include the hydrophobic material 132 on the surfaces thereof. In addition, one of each of the peaks 110 and each of the valleys 120 as well as the surface thereof may be formed of the hydrophobic material 132. The other one of the peaks 110 and the valleys 120 that do not include the hydrophobic material 132 on the surface thereof between each of the peaks 110 and each of the valleys 120 may include a hydrophilic material 134 on the surface thereof. For example, as illustrated in FIG. 6, when the peaks 110 include the hydrophobic material 132, the valleys 120 may include the hydrophilic material 134 on the surfaces thereof. In FIG. 6, it is illustrated that the peaks 110 include the hydrophobic material 132 on the surfaces thereof and the valleys 120 include the hydrophilic material 134 on the surfaces thereof. However, exemplary embodiments are not limited thereto. For example, the peaks 110 and the valleys 120 may be respectively formed of the hydrophobic material 132 and the hydrophilic material 134. According to exemplary embodiments, the hydrophobic material 132 may include polydimethylsiloxane (PDMS), SU-8 photoresist, etc. In addition, the hydrophilic material 134 may include $SiO_2$, $TiO_2$, etc. However, exemplary embodiments are not limited thereto.

As illustrated in FIG. 6, when one of each of the peaks 110 and each of the valleys 120 includes the hydrophobic material 132 and the other one of each of the peaks 110 and each of the valleys 120 includes the hydrophilic material 134, the target material may be more easily adsorbed onto one of each of the peaks 110 and each of the valleys 120. For example, when the target material includes oil, the oil may be easily physisorbed onto the hydrophobic material 132. Therefore, the target material that includes the oil may be easily adsorbed onto the peaks 110 that include the hydrophobic material 132 and may not be easily adsorbed onto the valleys 120 that include the hydrophilic material 134. Therefore, when a cross-section of the grating pattern element 100 is formed as illustrated in FIG. 6, when the grating pattern element 100 contacts the surface of the object 10 that includes the oil, the oil is easily adsorbed onto the peaks 110 and is not easily adsorbed onto the valleys 120 so that the height difference between the peaks 110 and the valleys 120 may change.

In the above, the grating pattern element 100 according exemplary embodiments were described with reference to FIGS. 1 to 6. When the above-described grating pattern element 100 contacts the surface of the object 10, the target material 20 provided on the surface of the object 10 is adsorbed onto the grating pattern element 100 so that the height difference between the peaks 110 and the valleys 120 of the grating pattern element 100 may change. Since the height difference is dependent on the amount of the target material 20, the grating pattern element 100 may be used for measuring the amount of the target material 20 provided on the surface of the object 10. Hereinafter, a target material measuring apparatus for measuring the amount of the target material 20 by using the above-described grating pattern element 100 will be described.

Figure 7:
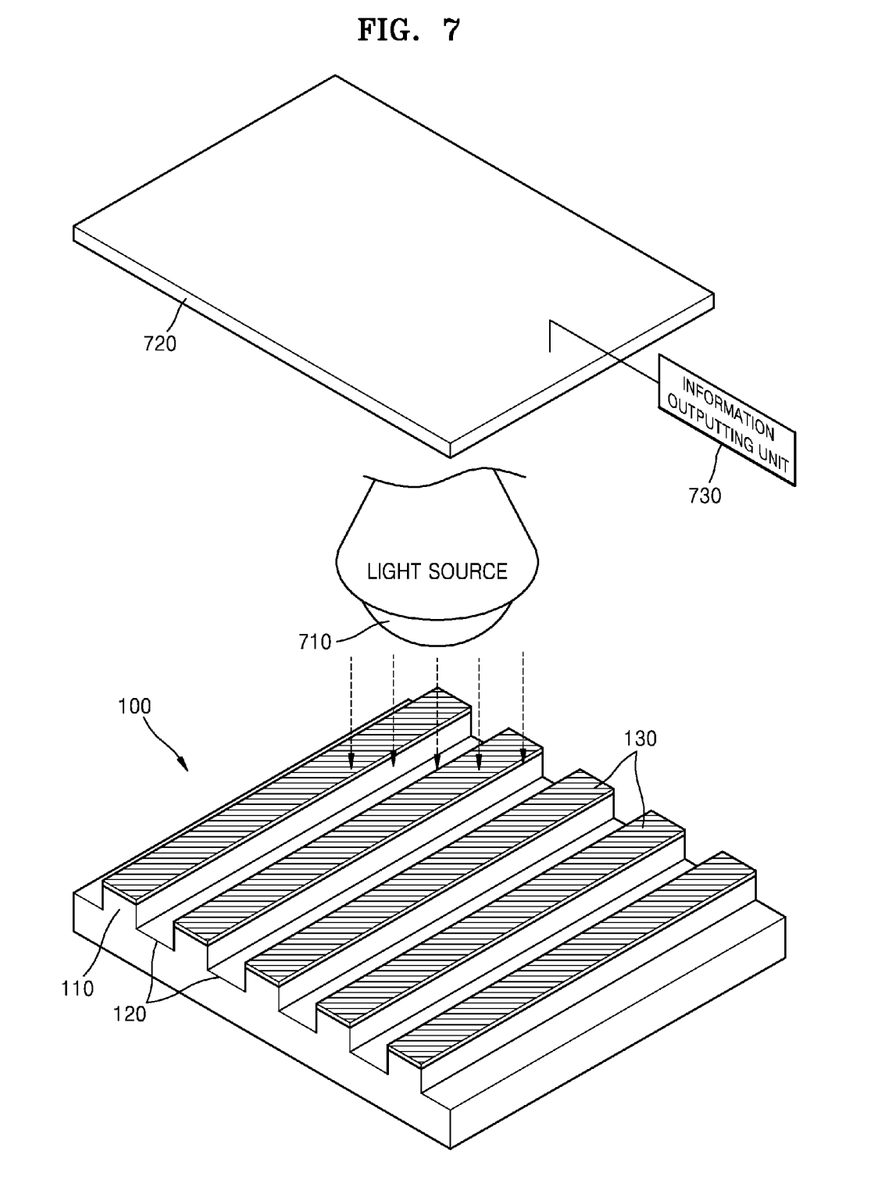
FIG. 7 is a view illustrating a target material measuring apparatus according to an exemplary embodiment.

FIG. 7 is a view illustrating a target material measuring apparatus 700 according to an exemplary embodiment. Referring to FIG. 7, the target material measuring apparatus 700 may include the grating pattern element 100 illustrated in FIGS. 1 to 6. That is, the target material measuring apparatus 700 may include the grating pattern element 100 including a concavo-convex cross-section in which the peaks 110 and valleys 120 are periodically arranged. Here, at least one of each of the peaks 110 and each of the valleys 120 may include the adsorbing material 130 which adsorbs the target material 20 on the surface thereof. Any of the exemplary embodiments illustrated in FIGS. 1 to 6 may be applied to the grating pattern element 100 illustrated in FIG. 7. Therefore, the height of the peaks 110 or the valleys 120 may change due to adsorption between the adsorbing material 130 and the target material 20.

The target material measuring apparatus 700 may include a light source 710 that irradiates the grating pattern element 100 with light. The light source 710 may emit light with a short wavelength. For example, the light source 710 may be a laser generating apparatus. However, exemplary embodiments are not limited thereto. The light source 710 may emit light components with various wavelengths. For example, a plurality of light sources 710 are provided so that the light sources may respectively emit light components with different wavelengths. In this case, the light source 710 that emits light may be controlled as occasion demands. The light emitted from the light source 710 may form diffraction patterns 200 by the grating pattern element 100. The height difference between the peaks 110 and the valleys 120 may be smaller than ¼ of the wavelength of the light emitted by the light source 710, which is for facilitating analysis of the diffraction patterns 200. Here, the height difference may represent the height difference after the target material 20 is adsorbed onto the adsorbing material 130 as well as the height difference before the target material 20 is adsorbed onto the adsorbing material 130. Shapes or intensities of the diffraction patterns 200 may change in accordance with the height difference between the peaks 110 and the valleys 120 of the grating pattern element 100.

The target material measuring apparatus 700 may include a measuring unit 720 for measuring the diffraction pattern 200 intensities of the light diffracted by the grating pattern element 100. The measuring unit 720 may be arranged in the same direction as or in an opposite direction to the light source 710 to be separated from the grating pattern element 100. The measuring unit 720 may measure at least one of intensities of constructive interference patterns shown in the diffraction patterns 200. For this purpose, the measuring unit 720 may include at least one light sensor (not shown).

Figure 8:
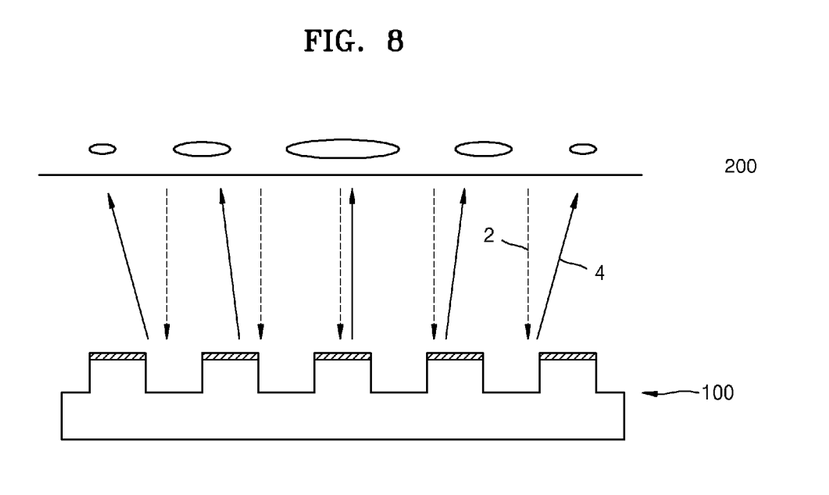
FIGS. 8 and 9 are views illustrating examples in which light emitted from the light source forms diffraction patterns by the grating pattern element.
Figure 9:
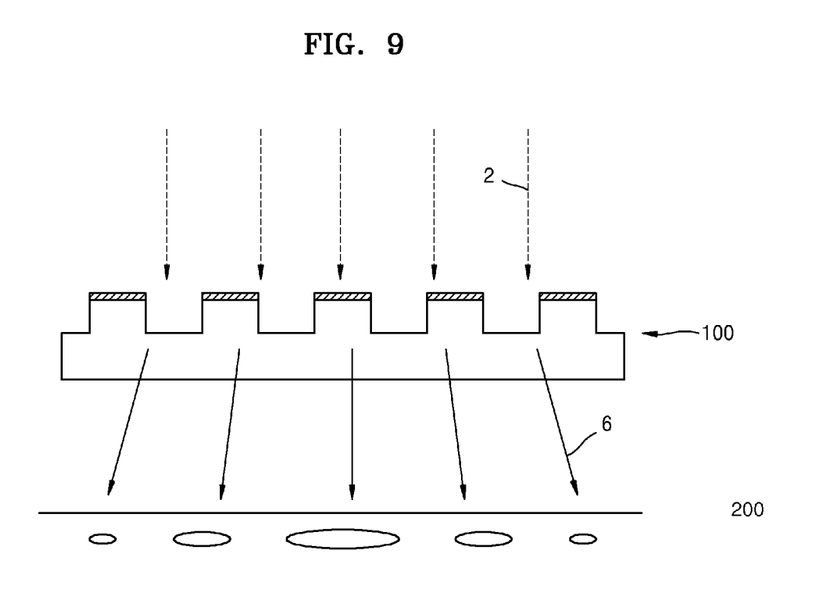

FIGS. 8 and 9 are views illustrating exemplary embodiments in which light 2 emitted from the light source 710 forms diffraction patterns 200 by the grating pattern element 100. Referring to FIG. 8, the light 2 emitted from the light source 710 is reflected by the grating pattern element 100 and may form the diffraction patterns 200. In this case, the grating pattern element 100 may include an opaque material that easily performs reflection. Reflected light 4 emitted from the grating pattern element 100 may form the diffraction patterns 200. In this case, the measuring unit 720 may be arranged above the grating pattern element 100, on a side of the grating pattern element 100 which is the same as the light source 710. Referring to FIG. 9, the light 2 emitted from the light source 710 passes through the grating pattern element 100 and may form the diffraction patterns 200. In this case, the grating pattern element 100 may include a transparent material. Transmitted light 6 emitted from the grating pattern element 100 may form the diffraction patterns 200. Therefore, in this case, the measuring unit 720 may be arranged below the grating pattern element 100, on a side of the grating pattern element 100 opposite the light source 710.

An information outputter 730 may output information indicating the amount of the target material 20 provided on the surface of the object 10 from the diffraction pattern 200 intensities measured by the measuring unit 720. The information outputter 730 may analyze how much of the target material 20 is adsorbed onto the adsorbing material 130 from the diffraction pattern 200 intensities measured by the measuring unit 720. Exemplary embodiments of this analysis are described herein.

Figure 10:
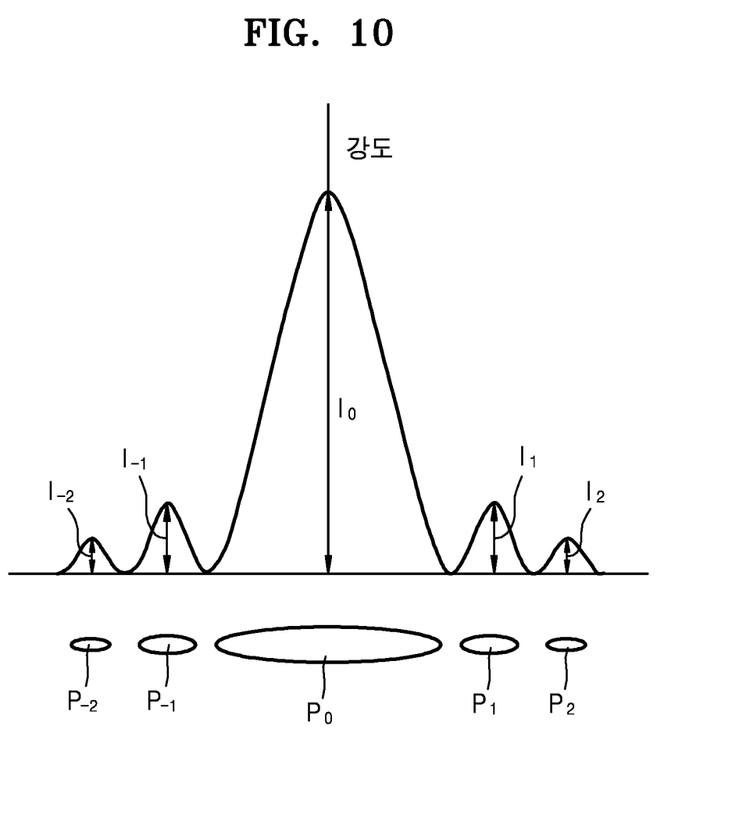
FIG. 10 is a view illustrating the diffraction pattern intensities measured by the measuring unit.

FIG. 10 is a view illustrating the diffraction pattern 200 intensities measured by the measuring unit 720. Referring to FIG. 10, a plurality of constructive interference patterns may be measured by the measuring unit 720. A pattern $P_0$ with the largest intensity is formed in the constructive interference patterns and constructive interference patterns $P_{-1}$, $P_1$, $P_{-2}$, $P_2$, . . . may be symmetrically formed. $P_n$ is a pattern separated from the central constructive interference pattern $P_0$ with the largest intensity by n. As an absolute value of n increases, the intensity of the pattern is reduced. When the intensity of $P_n$ is $I_n$, $I_n$ may satisfy EQUATION 1.

$$I_n \propto \cos^2(2\pi h/\lambda) \ldots (n=2j, j \text{ is an integer})$$

$$I_n \propto \sin^2(2\pi h/\lambda) \ldots (n=2j+1, j \text{ is an integer}) \quad \text{[EQUATION 1]}$$

where, h is the height difference between the peaks 110 and the valleys 120 and λ represents the wavelength of the light emitted from the light source 710.

As illustrated in EQUATION 1, $I_n$ may be proportional to a trigonometric function of the height difference h between the peaks 110 and the valleys 120. At this time, a proportional coefficient before the trigonometric function may vary in accordance with the intensity of the light emitted by the light source 710, light reflectance or transmittance of the grating pattern element 100, a distance between the grating pattern element 100 and the light source 710, and a distance between the grating pattern element 100 and the measuring unit 720. Therefore, when the other variables with respect to the proportional coefficient are uniform, $I_n$ may be dependent on only the height difference h between the peaks 110 and the valleys 120. As described above, h may vary in accordance with the amount of the target material 20 adsorbed onto the adsorbing material 130. Therefore, the amount of the target material 20 adsorbed onto the adsorbing material 130 may be determined by measuring $I_n$ so that it is possible to know how much of the target material 20 exists on the surface of the object 10.

The information outputter 730 may extract information indicating the height difference h between the peaks 110 and the valleys 120 by using a relationship between the EQUATION 1 and the intensity $I_n$ of $P_n$ with respect to an arbitrary n value. However, in this case, as described above, the proportional coefficient may vary in accordance with the intensity of the light emitted by the light source 710, the light reflectance or transmittance of the grating pattern element 100, the distance between the grating pattern element 100 and the light source 710, and the distance between the grating pattern element 100 and the measuring unit 720. That is, when the variables are correctly controlled, noise may be generated. In order to reduce error caused by the noise, the information outputter 730 may use a relationship between at least two constructive interference pattern intensities $I_n$ and EQUATION 1 with respect to different n values.

For example, the information outputter 730 may calculate an intensity ratio $I_n/I_m$ with respect to different n and m values from the measuring result of the measuring unit 720. At this time, absolute values of n and m may be different. The information outputter 730 may determine the height difference h between the peaks 110 and the valleys 120 by using the intensity ratio $I_n/I_m$ and EQUATION 1. In this case, in a process of obtaining the intensity ratio, proportional coefficients that are not defined in EQUATION 1 with respect to the different n and m are divided so that effects caused by the noise may be offset. Therefore, the height difference h between the peaks 110 and the valleys 120 may be correctly calculated by comparing the two or more intensity ratios. The information indicating the amount of the target material 20 may be correctly output by correctly calculating h.

In the intensity ratio $I_n/I_m$, when n and m are appropriately selected, the height difference h may be easily calculated. For example, when n=2i+1 (i is an integer) and m=2j (j is an integer), the intensity ratio $I_n/I_m$ satisfies EQUATION 2.

$$I_n/I_m \propto \tan^2(2\pi h/\lambda) \ldots (n=2i, m=2j+1; i \text{ and } j \text{ are integers})$$

The height difference h between the peaks 110 and the valleys 120 may be obtained from the $I_n/I_m$ value and EQUATION 2. The information outputter 730 may obtain the amount of the target material 20 adsorbed onto the adsorbing material 130 from the height difference h. The information outputter 730 may output the information indicating the amount of the target material 20 provided on the surface of the object 10 from the amount of the adsorbed target material 20.

According to exemplary embodiments, the target material measuring apparatus 700 was described with reference to FIGS. 7 to 10. Hereinafter, a method of measuring the target material 20 by using the target material measuring apparatus 700 will be described.

Figure 11:
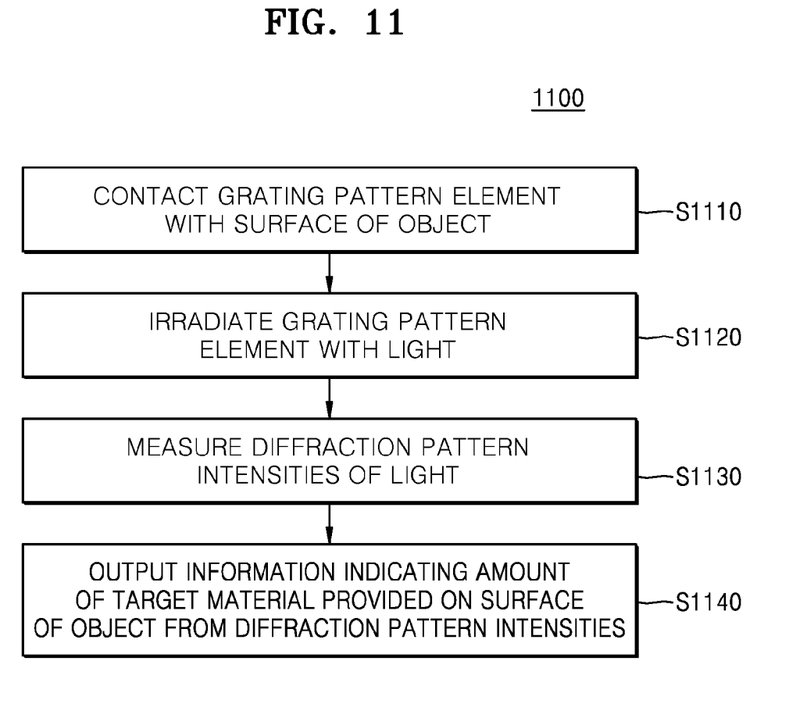
FIG. 11 is a flowchart of a target material measuring method according to an exemplary embodiment.

FIG. 11 is a flowchart of a target material measuring method 1100 according to an exemplary embodiment. Referring to FIG. 11, the target material measuring method 1100 may include contacting the grating pattern element 100 with the surface of the object 10 in operation S1110, irradiating the grating pattern element 100 with light in operation S1120, and measuring the diffraction pattern 200 intensities of the light diffracted by the grating pattern element 100 in operation S1130. Here, all the exemplary embodiments described with reference to FIGS. 1 to 6 may be applied to the grating pattern element 100.

The grating pattern element 100 may include the concavo-convex cross-section in which the peaks 110 and valleys 120 are periodically arranged. At least one of each of the peaks 110 and each of the valleys 120 may include the adsorbing material 130 which adsorbs the target material 20 on the surface thereof. The adsorbing material 130 may be physisorbed or chemisorbed onto the target material 20. The target material 20 may include at least one of the oil, the antigen, the antibody, and the heavy metals. However, exemplary embodiments are not limited thereto. For example, one of each of the peaks 110 and each of the valleys 120 may include the hydrophobic material 132 on the surface thereof and the other one may include the hydrophilic material 134 on the surface thereof. In addition, the height difference between the peaks 110 and the valleys 120 may be smaller than ¼ of the wavelength of the light emitted in the operation S1120 of emitting the light.

In the operation S1120 of emitting the light, monochromatic light may be emitted. However, exemplary embodiments are not limited thereto. In the measuring operation S1130, the intensity of at least one of the plurality of constructive interference patterns included in the diffraction patterns 200 may be measured. For example, in the measuring operation S1130, intensity of a 2nth (n is an integer) constructive interference pattern and intensity of a (2m+1)th (m is an integer) constructive interference pattern may be measured.

The target material measuring method 1100 may include information outputting operation S1140 of outputting the information indicating the amount of the target material 20 provided on the surface of the object 10 from the diffraction pattern 200 intensities. In the information outputting operation S1140, the height difference h between the peaks 110 and the valleys 120 may be calculated. The information outputting operation S1140 may use EQUATION 1 and the EQUATION 2 to calculate the height difference h between the peaks. In the information outputting operation S1140, the information indicating the amount of the target material 20 may be output from the calculated height difference h.

Figure 12:
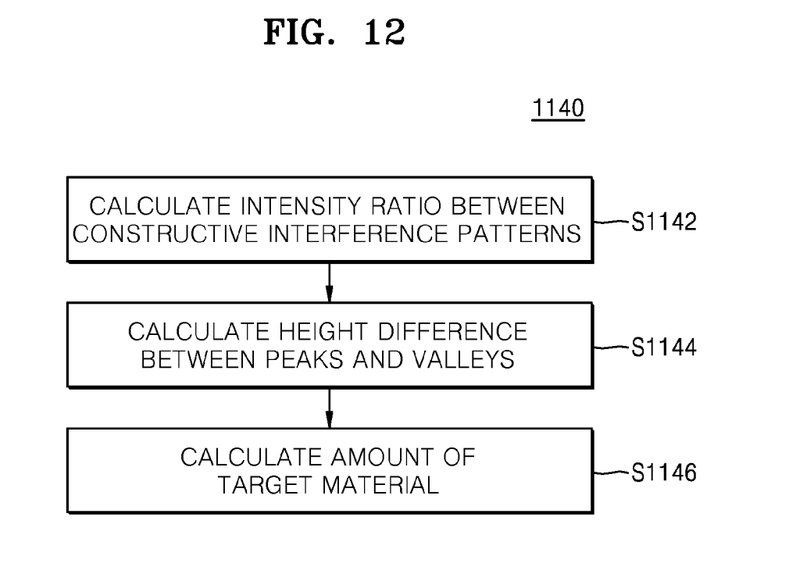
FIG. 12 is a flowchart exemplarily illustrating the information outputting operation of FIG. 11.

FIG. 12 is a flowchart exemplarily illustrating the information outputting operation S1140 of FIG. 11.

Referring to FIG. 12, the information outputting operation S1140 may include operation S1142 of calculating an intensity ratio between the constructive interference patterns. At this time, the intensity ratio between the constructive interference patterns may be the intensity ratio $I_n/I_m$ with respect to the different n and m as described above. The integers n and m may be selected to satisfy n=2i+1 (i is an integer) and m=2j (j is an integer). The information outputting operation S1140 may include calculating the height difference h between the peaks 110 and the valleys 120 from the intensity ratio $I_n/I_m$ in the height difference calculation operation S1144. In operation S1144, EQUATIONS 1 and 2 may be used. The information outputting operation S1140 may include calculating how much of the target material 20 is provided on the surface of the object 10 from the calculated height difference h in operation S1146. That is, calculating the amount of the target material 20 in operation S1146 may output information in which a user may be interested, that is, information indicating how much of the target material 20 is provided on the object 10.

The grating pattern element 100, the target material measuring apparatus 700, and the target material measuring method 1100 according to exemplary embodiments were described with reference to FIGS. 1 to 12. According to the exemplary embodiments, when the grating pattern element 100 contacts the surface of the object 10, the target material 20 may be adsorbed onto the adsorbing material 130. Therefore, the height difference between the peaks 110 and the valleys 120 of the grating pattern element 100 may change. The change in height difference may be determined by measuring the intensities of the diffraction patterns 200 generated by irradiating the grating pattern element 100 with light. The information indicating how much of the target material 20 is provided on the object 10 may be output from the information indicating the height difference.

The grating pattern element 100, the target material measuring apparatus 700, and the target material measuring method 1100 according to exemplary embodiments may be applied to various fields. The grating pattern element 100, the target material measuring apparatus 700, and the target material measuring method 1100 according to exemplary embodiments may be applied to analyzing how much target materials exist on surfaces of various objects. For example, the grating pattern element 100, the target material measuring apparatus 700, and the target material measuring method 1100 according to exemplary embodiments may be applied to detecting how much oil or other secretions exist on the skin of a human body, amounts of heavy metals, and amounts of an antigen and an antibody. However, exemplary embodiments are not limited thereto. The grating pattern element 100, the target material measuring apparatus 700, and the target material measuring method 1100 according to exemplary embodiments may be applied to a medical device for analyzing a surface of a skin and may be further applied to a health management system or a health care product through analysis of secretions on the surface of the skin.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An apparatus for measuring an amount of a target material provided on a surface of an object, the apparatus comprising:
   a grating pattern element including a concavo-convex cross-section in which peaks and valleys are periodically arranged and at least one of the peaks and at least one of the valleys comprises an adsorbing material which adsorbs the target material provided on a surface thereof;
   a light source configured to emit light and irradiate the grating pattern element with the light;
   a measuring unit configured to measure intensities of diffraction patterns of light diffracted by the grating pattern element; and
   an information outputter configured to output information indicating the amount of the target material provided on the surface of the object based on the intensities of the diffraction patterns of the diffracted light
   wherein the information outputter comprises a processor and a software program instructing the processor to calculate a height difference between the peaks and the valleys based on the intensities of the diffraction patterns.

2. The target material measuring apparatus of claim 1, wherein one of the peaks and of the valleys comprises a hydrophobic material provided on a surface thereof and the other one of the peaks and of the valleys comprises a hydrophilic material provided on a surface thereof.

3. The target material measuring apparatus of claim 1, wherein the measuring unit measures at least one of intensities of a plurality of constructive interference patterns included in the diffraction patterns.

4. The target material measuring apparatus of claim 3, wherein the information outputter calculates an intensity ratio between two different constructive interference patterns among the plurality of constructive interference patterns.

5. The target material measuring apparatus of claim 4, wherein one of the two different constructive interference patterns is a (2m+1)th constructive interference pattern and the other is a 2nth constructive interference pattern, wherein m and n are integers.

6. The target material measuring apparatus of claim 1, wherein a height difference between the peaks and the valleys is smaller than ¼ of a wavelength of the light emitted by the light source.

7. A target material measurement method comprising:
contacting a surface of an object with a grating pattern element including a concavo-convex cross-section in which peaks and valleys are periodically arranged and at least one of each of the peaks and each of the valleys includes an adsorbing material which adsorbs the target material provided on a surface thereof;
irradiating the grating pattern element with light;
measuring intensities of diffraction patterns of light diffracted by the grating pattern element; and
outputting information indicating the amount of the target material provided on the surface of the object based on the intensities of the diffraction patterns of the diffracted light
wherein the outputting of the information indicating the amount of the target material provided on the surface of the object from the intensities of the diffraction patterns of the diffracted light comprises calculating a height difference between the peaks and the valleys based on the intensities of the diffraction patterns.

8. The target material measuring method of claim 7, wherein the target material is physisorbed or chemisorbed onto the adsorbing material.

9. The target material measuring method of claim 7, wherein the measuring of intensities of diffraction patterns of light diffracted by the grating pattern element comprises measuring intensities of at least one of a plurality of constructive interference patterns included in the diffraction patterns.

10. The target material measuring method of claim 9, wherein the calculating further comprises calculating an intensity ratio between two different constructive interference patterns among the plurality of constructive interference patterns.

11. The target material measuring method of claim 7, wherein a height difference between the peaks and the valleys is smaller than ¼ of a wavelength of the light used to irradiate the grating pattern element.

* * * * *